(12) United States Patent
Soto Santos (10) Patent No.: US 10,410,744 B2
(45) Date of Patent: Sep. 10, 2019

(54) SYSTEM AND METHOD OF PRINTING MACHINE-READABLE INFORMATION USABLE IN A MEDICAL PROCEDURE

(71) Applicant: Novartis AG, Basel (CH)

(72) Inventor: Samuel Soto Santos, Berlin (DE)

(73) Assignee: Novartis AG (CH)

( * ) Notice: Subject to any disclaimer, the term of this patent is extended or adjusted under 35 U.S.C. 154(b) by 0 days.

(21) Appl. No.: 15/743,629

(22) PCT Filed: Jan. 20, 2017

(86) PCT No.: PCT/IB2017/050320
§ 371 (c)(1),
(2) Date: Jan. 10, 2018

(87) PCT Pub. No.: WO2018/134644
PCT Pub. Date: Jul. 26, 2018

(65) Prior Publication Data
US 2019/0027239 A1    Jan. 24, 2019

(51) Int. Cl.
*G16H 10/65* (2018.01)
*G16H 40/20* (2018.01)
*G06K 19/06* (2006.01)

(52) U.S. Cl.
CPC ....... *G16H 10/65* (2018.01); *G06K 19/06028* (2013.01); *G06K 19/06037* (2013.01); *G16H 40/20* (2018.01)

(58) Field of Classification Search
None
See application file for complete search history.

(56) References Cited

U.S. PATENT DOCUMENTS

| | | | | |
|---|---|---|---|---|
| 4,947,867 A | * | 8/1990 | Keeton | A61F 13/00059 128/846 |
| 7,389,928 B2 | * | 6/2008 | Lubow | G06K 17/00 235/462.01 |
| 2011/0029320 A1 | * | 2/2011 | Jamali | G06Q 50/22 705/2 |
| 2011/0307284 A1 | * | 12/2011 | Thompson | G06Q 10/06311 705/7.13 |

* cited by examiner

*Primary Examiner* — Kristy A Haupt
(74) *Attorney, Agent, or Firm* — Keiko Ichiye, Esq.

(57) ABSTRACT

The present disclosure provides a system able to acquire machine-readable information received from at least one of images received via the camera, process the machine-readable information to determine patient data from the machine-readable information, determine a medical procedure based on the patient data, permit use of at least a first portion of medical equipment coupled to the system, receive user input that indicates at least one planned procedure step, determine if the medical procedure includes the at least one planned procedure step. The present disclosure further includes a method including the above steps. The present disclosure also includes a system for printing machine-readable information on a garment to be worn in a medical procedure and a method of printing machine-readable information on such a garment.

18 Claims, 8 Drawing Sheets

SYSTEM AND METHOD OF PRINTING MACHINE-READABLE INFORMATION USABLE IN A MEDICAL PROCEDURE

CROSS REFERENCE TO RELATED APPLICATIONS

This application is a section 371 national stage phase of International Application No. PCT/IB2017/050320, filed 20 Jan. 2017, titled "SYSTEM AND METHOD OF PRINTING MACHINE-READABLE INFORMATION USABLE IN A MEDICAL PROCEDURE," which is hereby incorporated by reference in its entirety.

BACKGROUND

Field of the Disclosure

This disclosure relates to quality assurance in medical procedures and more particularly to systems and methods for authenticating patient information with the medical procedure or process elements of the medical procedure.

Description of the Related Art

In the past, patients' information, such as patients' records, were usually printed on papers and not physically attached to the patients. This increased a likelihood of obtaining an incorrect patient's record. For example, when a patient moved from one location to another location, a likelihood of obtaining an incorrect patient's record increased. For instance, in some medical procedures, the patient moves from one medical facility (e.g., a doctor's office) to another medical facility (e.g., a surgical facility).

Moreover, as a number of process elements of a medical procedure increases and/or as increased lengths of time are interposed between two or more of the process elements of the medical procedure, the likelihood of an error can also increase. For example, each of the process elements of the medical procedure introduces its own chance of error, and as the number of the process elements of the medical procedure increases, so does the overall chance of error of the medical procedure.

In addition, a process of patient identification can introduce a possibility of error. For example, one or more portions of a patient may be concealed from sight during a medical procedure. For instance, one or more portions of the patient's face may be shrouded during a surgical procedure. This may also introduce a possibility of error via an incorrect orientation (e.g., a positioning) of one or more portions of the patient's body.

SUMMARY

The present disclosure provides a system including a printing device able to print machine-readable information upon a garment to be worn during a medical procedure, a processor communicatively coupled to the printing device, and a memory, coupled to the processor, that stores instructions executable by the processor. As the processor executes the instructions, the system is able to receive patient information associated with a patient, encode the patient information, producing encoded patient information, and place machine-readable information, based on the encoded patient information, on the garment to be worn by the patient during the medical procedure.

The present disclosure may further include a non-transient computer-readable memory device with instructions that, when implemented by a system, cause the system to perform the above steps.

The present disclosure further includes a system or a non-transient computer-readable memory device as described above with one or more of the following additional features, which may be used in combination with one another unless clearly mutually exclusive: i) the machine-readable information may include a barcode; ii) the barcode may be a two-dimensional barcode; iii) when the system encodes the patient information, producing the encoded patient information, the system may be able to produce at least one of a graphic, a raster, a bit-map, a scalar vector graphic, and instruction, and as the processor executes the instructions, the system may be further able to provide the at least one of the graphic, the raster, the bit-map, the scalar vector graphic, and the instructions to the printing device to print, based on the at least one of the graphic, the raster, the bit-map, the scalar vector graphic, and the instructions, the machine-readable information, based on the encoded patient information, on the garment to be worn by the patient during the medical procedure; iv) the machine-readable information may include information that indicates a medical procedure; v) the machine-readable information may include preoperative measurements; vi) the machine-readable information may include orientation information; vii) when the system encodes the patient information, producing the encoded patient information, the system may be able to encrypt at least a portion of the patient information; viii) as the processor executes the instructions, the system may be further able to print, via the printing device, intraoperative guidance information, based on the patient information, on the garment to be worn by the patient during the medical procedure; ix) the intraoperative guidance information may include at least one of a graphic and a depiction of at least one of a device and an implant to be used in the medical procedure.

The present disclosure also provides a method of printing a garment to be worn during a medical procedure by receiving patient information associated with a patient, encoding the patient information, producing encoded patient information, and printing, a printing device, machine-readable information, based on the encoded patient information, on a garment to be worn by the patient during a medical procedure.

The present disclosure further includes a system or a non-transient computer-readable memory device as described above with one or more of the following additional features, which may be used in combination with one another unless clearly mutually exclusive: i) the machine-readable information may include a barcode; ii) the barcode may be a two-dimensional barcode; iii) the encoding the patient information, producing the encoded patient information, may include producing at least one of a graphic, a raster, a bit-map, a scalar vector graphic, and instructions, and the method may further include providing the at least one of the graphic, the raster, the bit-map, the scalar vector graphic, and the instructions to the printing device to print, based on the at least one of the graphic, the raster, the bit-map, the scalar vector graphic, and the instructions, the machine-readable information, based on the encoded patient information, on the garment to be worn by the patient during the medical procedure; iv) the machine-readable information may include information that indicates a medical procedure; v) the machine-readable information may include preoperative measurements; vi) the machine-readable information may include orientation information; vii) the encoding the patient information, producing the encoded patient information, may include encrypting at least a portion of the patient information; viii) the method may further include disposing intraoperative guidance information, based on the patient information, on the garment to be worn by the patient during the medical procedure; ix) the intraoperative guidance information may include at least one of a graphic and a depiction of at least one of a device and an implant to be used in the medical procedure.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

In the following description, details are set forth by way of example to facilitate discussion of the disclosed subject matter. It should be apparent to a person of ordinary skill in the field, however, that this description is exemplary and not exhaustive of all possibilities.

As used herein, a reference numeral followed by a letter refers to a specific instance of an element and the numeral only form of the reference numeral refers to the collective element. Thus, for example, device '12a' refers to an instance of a device class, which may be referred to collectively as devices '12' and any one of which may be referred to generically as a device '12'.

Machine-readable information may be printed and/or placed on garments used in medical procedures. For example, the machine-readable information may include machine-readable markings that may be printed and/or placed on garments worn by patients and/or medical personnel. The machine-readable information may include patient and/or treatment information that may be printed and/or placed on garments worn by patients before, during, and/or after medical treatment to provide identification of the patient and/or to provide patient treatment information.

Using one or more data processing systems that process the machine-readable information may mitigate or eliminate some mistakes and/or errors before, during, and/or after medical treatment. For example, the machine-readable information may include one or more optical codes printed and/or placed on a garment worn by a patient for a medical procedure, and a device used by medical personnel can read the one or more optical codes. The one or more optical codes may indicate a medical treatment and prescribe and/or set an orientation of one or more of the patient, an implant, and a medical instrument, among others. The one or more optical codes may provide authentication information and/or be used in an authentication process that may mitigate and/or eliminate fraud.

The garments worn by the patients may be disposable, and the machine-readable information may be printed and/or placed on the disposable garments. For example, the machine-readable information may include one or more optical codes that may be printed and/or placed on the disposable garments. The garments worn by the patients may be reusable, and the machine-readable information may printed and/or placed on a medium and then adhered to the reusable garment. For example, one or more optical codes may be printed and/or placed on a paper, cloth, or plastic medium and fastened to the reusable garment with a fastener. The fastener may include an adhesive. The fastener may include one or more of a clip and a safety pin, among others.

Machine-readable information may aid and/or assist in treatment selection and/or application. In one example, one or more optical codes may indicate the medical procedure, and patient information may be retrieved and provided to one or more medical devices used in the medical procedure. In another example, The medical procedure may include an ocular medical procedure, and one or more of an image of a patient's eye, radii, a corneal curvature of steep and flat axes, a limbal position and diameter, a pupil position and diameter, and a corneal reflex position, among others, may be retrieved and/or provided to a surgical microscope to display reference and microscope images, which may allow a surgeon to account for lateral and rotational eye movements.

Figure 1:
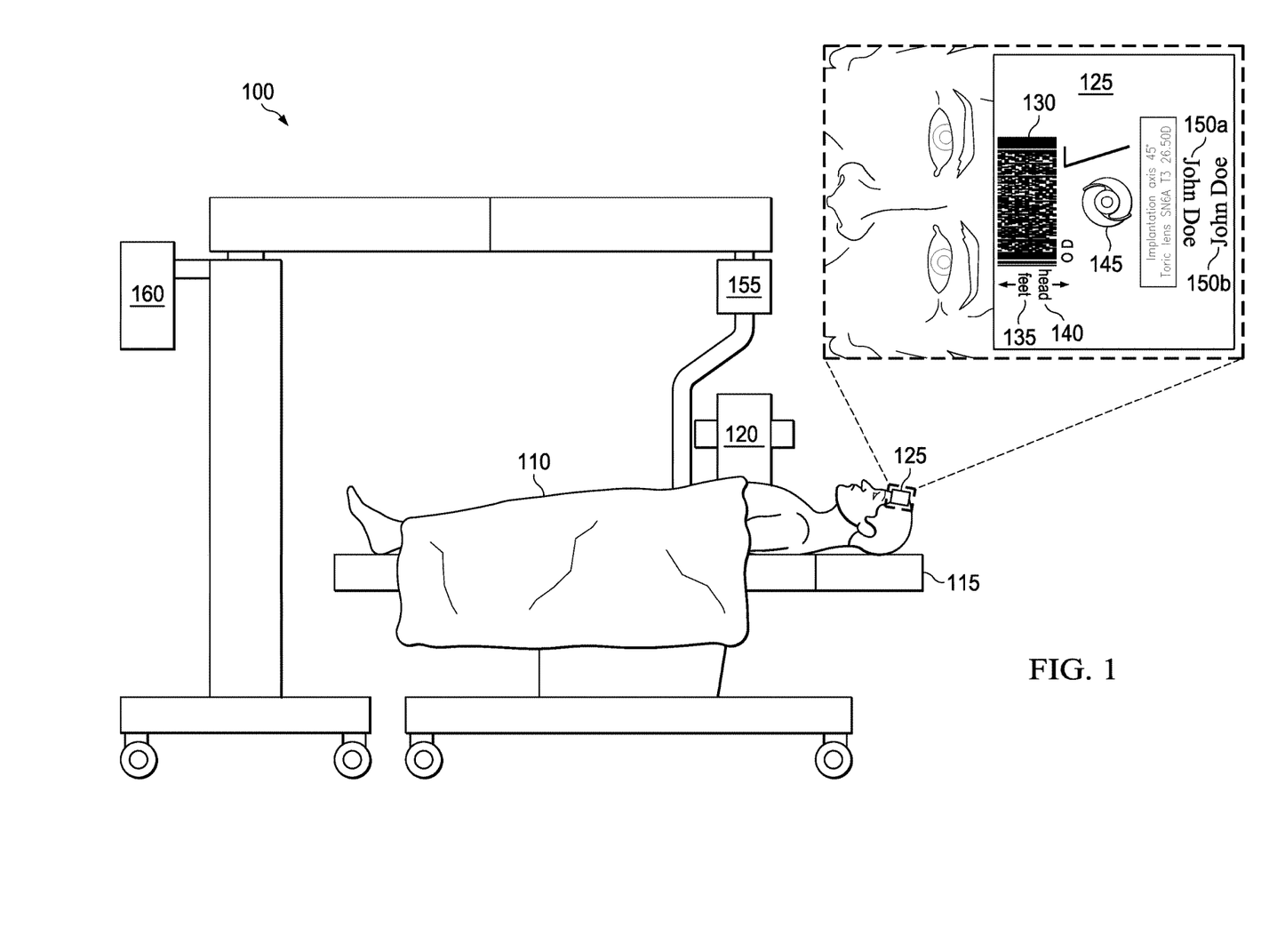
FIG. 1 illustrates a medical system that may be used in medical procedures, according to one or more embodiments.

Turning now to the figures, FIG. 1 illustrates a medical system 100 that may be used in medical procedures, according to one or more embodiments. Although FIG. 1 includes particular medical equipment, medical system 100 may include less equipment or may include addition equipment. For example, medical system 100 may be configured for one or more particular medical procedures that may not use equipment illustrated and/or that may involve other equipment that is not specifically illustrated.

As shown, a patient 110 may be supported via a table 115. Although table 115 is illustrated as a mobile table, table 115 may be fixed to a floor or may be substantially fixed to the floor (e.g., not readily moved). Patient 110 may be about to undergo a medical procedure. In one example, the medical procedure may include a cataract surgery. In a second example, the medical procedure may include a laser eye surgery. In another example, the medical procedure may include a corneal transplant. Although the disclosed examples of surgeries are not exhaustive, other types of surgeries may use the methods and systems disclosed herein.

As illustrated, medical system may include a microscope 120. Microscope 120 may be or include a microscope integrated display (MID). In one example, microscope 120 may augment one or more images of a patient with medical information that may be used during the medical procedure. In another, microscope 120 may display information to a surgeon or other medical personnel that may allow the surgeon or the other medical personnel to visualize patient medical data without disrupting a surgery.

Microscope 120 may include a camera. In one example, the camera may acquire one or more images of patient 110. In another example, the camera may acquire one or more images of a garment 125 worn by patient 110 and/or affixed to patient 110. As illustrated, garment 125 may be or include a headband worn by patient 110 and/or affixed to patient 110. Although garment 125 may be or include a headband, as shown, garment 125 may be or include other items and/or garments worn by patient 110 and/or affixed to patient. For example, garment 125 may be or include scrub pants, a bandage, a scrub shirt, one or more socks, one or more slippers, a patient gown, an exam cape, exam shorts, or a robe, among others.

Garment 125 may include machine-readable information 130 that is associated with patient 110. In one example, machine-readable information 130 may be or include machine-readable markings such as a barcode. The bar code may be a single dimensional barcode. The bar code may be a multi-dimensional barcode. In another example, machine-readable information 130 may be or include symbols. The symbols may be or include letters of a written language (e.g., English, German, French, Chinese, Russian, etc.) that may be processed via an optical character recognition (OCR) process and/or system.

Machine-readable information 130 may be used to store information associated with patient 110. In one example, the information associated with patient 110 may include identification information associated with patient 110. The identification information may include one or more of a name, a date of birth, and a government identification, among others. In a second example, the information associated with patient 110 may include medical information associated with patient 110. The medical information associated with patient 110 may include one or more of a medical procedure, a medication list, a portion of patient 110 that is a subject of a medical procedure, one or more drug allergies, a diagnosis, and an orientation of patient 110 for a medical procedure, among others. In another example, the information associated with patient 110 may include indexing information. The indexing information may be used to index into a database and/or a storage device that stores information associated with patient 110. The indexing information may be used as a key or used to create the key that may be used to retrieve information associated with patient 110 from a database and/or a storage device that stores the information associated with patient 110.

Machine-readable information 130 may be printed and/or placed as part of the patient record on any kind of support media format (e.g., paper, cloth, plastic card, sticker, etc.). For example, machine-readable information 130 may include a bar code and/or a custom optical code and/or marking. A device used in a medical setting may include a camera that can acquire machine-readable information 130, and the device may process machine-readable information 130 to select a patient treatment and/or a medical procedure.

The camera that can acquire machine-readable information 130 may include one or more digital image sensors that transform incoming photons into electrical charges and/or electrical signals. In one example, the one or more digital image sensors may include one or more charge-coupled devices (CCDs). In another example, the one or more digital image sensors may include one or more complementary metal-oxide-semiconductor (CMOS) devices.

As illustrated, garment 125 may include orientation information such as orientation information 135-145. As shown, orientation information 135 may aid in orienting garment 125, as to a proper direction of garment 125 with relation to feet of patient 125, and orientation information 140 may aid in orienting garment 125, as to a proper direction of garment 125 with relation to a head of patient 110. Although not specifically shown, garment 125 may include orientation information that indicates a front orientation or a rear orientation. As illustrated, garment 125 may include name information 150 that may be used in assigning garment 125 to patient 110. Although not specifically illustrated, other markings such as a date of birth may be used in assigning garment 125 to patient 110. Orientation information 145 may aid in orienting one or more of an instrument and an implant, among others, that is or are used in a medical procedure.

Although the orientation information illustrated may be specific in some aspects, the orientation information may be changed and/or oriented differently for one or more medical personnel. In one example, a first doctor may perform a surgery via a superior position. In a second example, a second doctor may perform a surgery via a temporal position, such as one side of patient 110 or another side of patient 110. In another example, a third doctor may perform a surgery via an oblique position, such as at any angle with reference to patient 110.

As shown, medical system 100 may include displays 155 and 160. Microscope 120 may include display 155. For example, display 155 may be or include a heads up display for microscope 120. Display 160 may display images acquired via microscope 120. For example, other medical personnel and/or medical students may use display 160 to view the images acquired via microscope 120. Display 160 may display information associated with patient 110. For example, display 160 may provide vital signs of patient 110.

A processor associated with medical system 100 may process machine-readable information 130 and determine if a medical procedure that uses medical system 100 is authorized and/or permitted. If the processor determines that the medical procedure that uses medical system 100 is authorized and/or permitted, the processor may permit use of medical system 100 for the medical procedure. If the processor determines that the medical procedure that uses medical system 100 is not authorized and/or not permitted, the processor may not permit functionality of one or more portions of medical system 100. In one example, the processor may not permit functionality of microscope 120 and/or display 155. In another example, while the processor may not permit functionality of microscope 120 and/or display 155, the processor may permit or continue to permit display 160 to provide vital signs of patient 110.

The processor associated with medical system 100 may process machine-readable information 130 and determine if an orientation of machine-readable information 130 is in accordance with one or more rules. For example, the one or more rules may stipulate that machine-readable information 130 is aligned in a specified way in relation to microscope 120. As machine-readable information 130 is attached to patient 110, the one or more rules may effectively stipulate that patient 110 is aligned in the specified way in relation to microscope 120. One or more alignment rules may include one or more of tilt, roll, azimuth, and yaw of machine-readable information 130 in relation to microscope 120.

As such, if the processor determines that the medical procedure that the orientation of machine-readable information 130 is in accordance with the one or more rules, the processor may permit use of medical system 100 for the medical procedure. If the processor determines that the orientation of machine-readable information 130 is not in accordance with the one or more rules, the processor may not permit functionality of one or more portions of medical system 100.

Figures 2A, 2B, 2C, 2D:
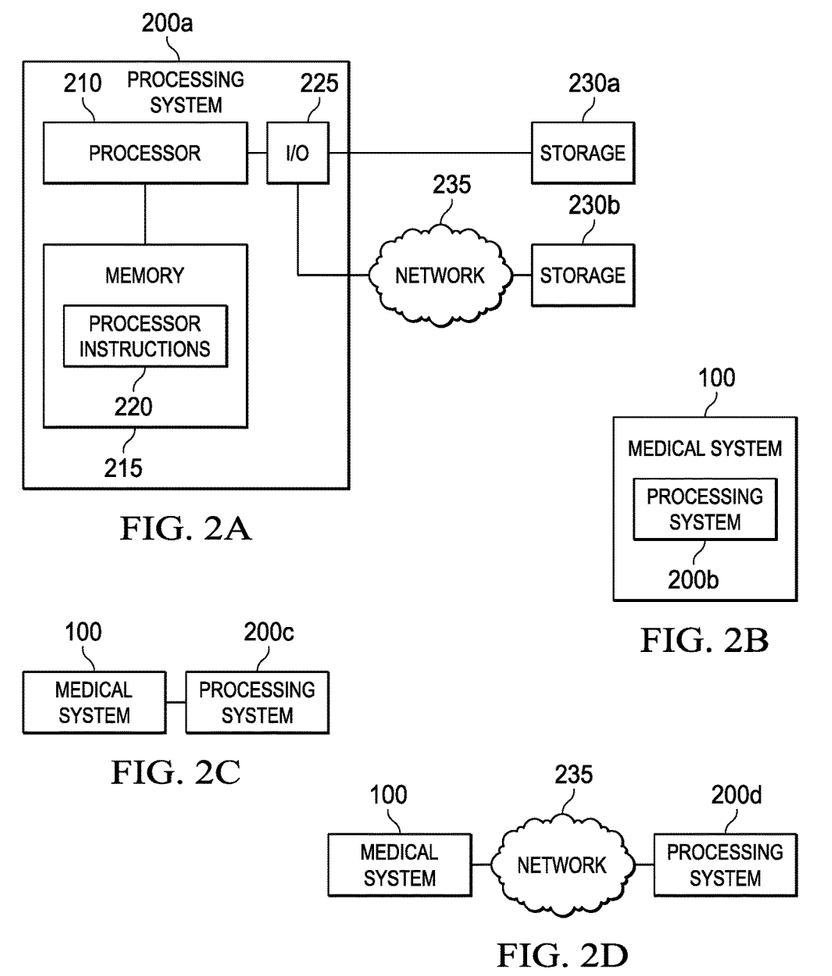
FIG. 2A illustrates a processing system, according to one or more embodiments.
FIG. 2B provides a block diagram of a medical system that includes a processing system, according to one or more embodiments.
FIG. 2C provides a block diagram of a medical system communicatively coupled to a processing system, according to one or more embodiments.
FIG. 2D provides a block diagram of a medical system communicatively coupled to a processing system via a network, according to one or more embodiments.

Turning now to FIG. 2A, a processing system 200 is illustrated, according to one or more embodiments. Although FIG. 2A includes particular elements, processing system 200 may include fewer elements or may include addition elements. As shown, processing system 200 may include a processor 210 and a memory 215, coupled to processor 210. Memory 215 may include persistent and volatile media, fixed and removable media, and magnetic and semiconductor media, among others. Memory 215 may include storage media such as non-transitory computer-readable media that stores data and instructions, such as executable code, for at least a period of time. Memory 215 may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, memory 215 may include processor instructions 220.

Processor 210 may execute processor instructions 220 to implement one or more systems, processes, and/or methods described herein. For example, processor instructions 220 may be configured, coded, and/or encoded with instructions in accordance with one or more of flowcharts, methods, and/or processes described herein. One or more of a storage medium and a memory medium may be a software product, a program product, and/or an article of manufacture. For example, the software product, the program product, and/or the article of manufacture may be configured, coded, and/or encoded with instructions, executable by a processor, in accordance with one or more of flowcharts, methods, and/or processes described herein.

Processor 210 may include any suitable system, device, or apparatus operable to interpret and execute program instructions, process data, or both stored in memory 215 and/or received via a network. Processor 210 further may include one or more microprocessors, microcontrollers, digital signal processors (DSPs), application specific integrated circuits (ASICs), or other circuitry configured to interpret and execute program instructions, process data, or both.

As illustrated, processor 210 may be communicatively coupled to an input/output (I/O) device 225. I/O device 225 may include any instrumentality or instrumentalities, which allow a user to interact with processing system 200 and its associated components by facilitating input from a user and output to a user. Facilitating input from a user may allow the user to manipulate processing system 200, and facilitating output to a user may allow processing system 200 to indicate effects of the user's manipulation. For example, I/O device 225 may allow a user to input data, instructions, or both into processing system 200, and otherwise manipulate processing system 200 and its associated components. I/O devices may include user interface devices, such as a keyboard, a mouse, a touch screen, a joystick, a handheld lens, a tool tracking device, a coordinate input device, or any other I/O device suitable to be used with a medical system, such as medical system 100 (see FIG. 1).

I/O device 225 may include one or more busses, one or more serial devices, and/or one or more network interfaces, among others, that may facilitate and/or permit processor 210 to implement one or more systems, processes, and/or methods described herein. In one example, I/O device 225 may include a storage interface that may facilitate and/or permit processor 210 to communicate with an external storage 230a. The storage interface may include one or more of a universal serial bus (USB) interface, a SATA (Serial ATA) interface, a PATA (Parallel ATA) interface, and a small computer system interface (SCSI), among others. In a second example, I/O device 225 may include a network interface that may facilitate and/or permit processor 210 to communicate with a network 235. I/O device 225 may include one or more of a wireless network interface and a wired network interface. In another example, I/O device 225 may include one or more of a peripheral component interconnect (PCI) interface, a PCI Express (PCIe) interface, a serial peripheral interconnect (SPI) interface, and an inter-integrated circuit ($I^2C$) interface, among others.

As shown, a storage 230b may be coupled to network 235. Processor 210 may access storage 230b via network 235. For example, processor 210 may store data via storage 230b and/or retrieve data via storage 230b. Processor 210 may store information associated with patient 110 (see FIG. 1) via storage 230b and/or retrieve information associated with patient 110 via storage 230b.

Network 235 may include one or more networks. In one example, network 235 may include a local area network (LAN). In a second example, network 235 may include and/or form a portion of a wide area network (WAN). Network 235 may include and/or form a portion of an Internet. In another example, network 235 may include one or more of a wired and a wireless network.

Network 235 may be coupled to one or more networks. In one example, network 235 may be coupled to a public switch telephone network (PSTN). In another example, network 235 may coupled to a public WAN. The public WAN may include the Internet.

Turning now to FIGS. 2B-2D, various configurations of medical system 100 and processing system 200 are illustrated, according to one or more embodiments. As shown in FIG. 2B, medical system 100 (see FIG. 1) may include processing system 200. Processing system 200 may be communicatively coupled to one or more portions of medical system 100. For example, processor 210 may control and/or provide access control to one or more portions of medical system 100. Processor 210 may be communicatively coupled to one or more portions of medical system 100 via I/O device 225 to control and/or provide access control to one or more portions of medical system 100.

Processing system 200 may be external to medical system 100, and medical system 100 (see FIG. 1) may be communicatively coupled to processing system 200. As illustrated in FIGS. 2C and 2D, processing system 200 can be external to medical system 100. In one example, processing system 200 may be communicatively coupled to medical system 100 via I/O device 225, as shown in FIG. 2C. In another example, processing system 200 may be communicatively coupled to medical system 100 via network 235, illustrated in FIG. 2D.

Figure 3A:
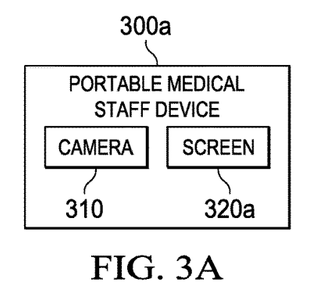
FIG. 3A provides a block diagram of a portable medical staff device that includes a camera, according to one or more embodiments.
Figure 3B:
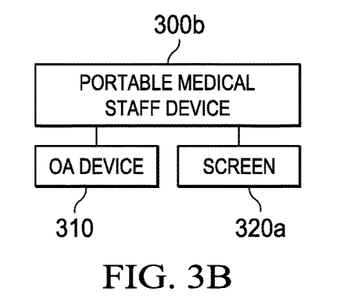
FIG. 3B provides a block diagram of a portable medical staff device communicatively coupled to an optical acquisition device, according to one or more embodiments.

Turning now to FIGS. 3A and 3B, a portable medical staff device 300 is illustrated, according to one or more embodiments. As shown in FIG. 3A, portable medical staff device 300a can include a camera 310 and a screen 320a. As shown in FIG. 3B, a portable medical device 300b may be coupled to one or more of an optical acquisition (OA) device 330 and a screen 320b. OA device 330 may be or include one or more of a camera and an optical code reader, among others. In one example, OA device 330 may be coupled to portable medical device 300b in a wired fashion. In another example, OA device 330 may be coupled to portable medical device 300b in a wireless fashion.

Portable medical staff device 300 may be used to acquire machine-readable information 130 via camera 310 (see FIG. 3A) or via OA device 330 (see FIG. 3B). In one example, portable medical staff device 300 may facilitate and/or permit one or more medical staff to verify that machine-readable information 130 is associated with patient 110. Screen 320a may provide identification information such as a name, a date of birth, etc., based on machine-readable information 130, and the one or more medical staff may verify that information with patient 110 or a medical proxy of patient 110. In another example, portable medical staff device 300 may facilitate and/or permit one or more medical staff to route a patient through a medical facility. Screen 320 may provide routing information (e.g., destination location, etc.) based on machine-readable information 130.

Portable medical staff device 300 may provide information retrieved from machine-readable information 130 and/or retrieved from a database. In one example, machine-readable information 130 may include encoded markings, and portable medical staff device 300 may process machine-readable information 130 and provide some or all information that was encoded. In another example, portable medical staff device 300 may retrieve information from a database and/or a storage device, based on machine-readable information 130, and provide the retrieved information via screen 320. The database and/or the storage device may be local to portable medical staff device 300. Portable medical staff device 300 may access the database and/or the storage device via a network (e.g., network 235).

Portable medical staff device 300 may include any type of portable processing device. For example, portable medical staff device 300 may include a personal digital assistant (PDA), a laptop computer system, a wireless telephonic device, a tablet computing device, and a mobile computing system, among others.

Figure 4:
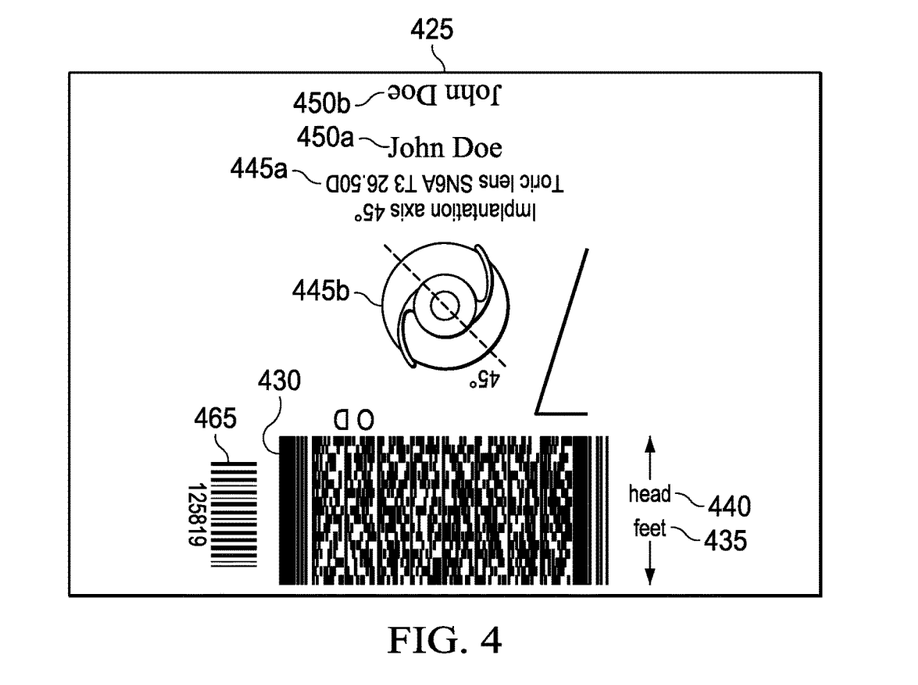
FIG. 4 illustrates a garment embodied as a headband that includes machine-readable information, according to one or more embodiments.

Turning now to FIGS. 4-7, various garments with machine-readable information are illustrated, according to one or more embodiments. FIG. 4 shows a garment 425 embodied as a headband that may be worn by patient 110 (see FIG. 1). As shown, garment 425 may include a name 450 and machine-readable information 430 that is associated with patient 110. Machine-readable information 430 may be or include a two-dimensional barcode. For example, the two-dimensional barcode may be or include a PDF417 barcode, which is a stacked linear barcode symbol format.

Machine-readable information 430 may include, for example, one or more of a name, a date of birth, a type of surgery, a checksum of at least a portion of information associated with patient 110 (see FIG. 1), one or more locations, and medical procedure information, among others. Machine-readable information 430 may include a comma-separated value string, such as "John Doe, 9 Jan. 1955, cataract, 3626EE2F, OR7, RR6B, axis 45, toric lens, SN6A T3 26.50D". For example, "cataract" is the type of surgery, "3626EE2F" is a checksum (e.g., a thirty-two bit cyclic redundancy check) of "OR7, RR6B, axis 45, toric lens, SN6A T3 26.50D", and "axis 45", "toric lens", "SN6A T3 26.50D" may be information for medical personnel associated with the medical procedure.

One or more portions of information associated with patient 110 may be encrypted. For example, "John Doe, 9 Jan. 1955, cataract, 3626EE2F" may be encrypted. Using encryption of one or more portions of patient information may facilitate and/or permit compliance with one or more policies, one or more rules, one or more regulations, and/or one or more laws. Using encryption of one or more portions of patient information may facilitate and/or permit authentication of the one or more portions of patient information.

As shown, machine-readable information 430 includes a barcode generated via a string "LzEsJkbW8xdf70vF+7wTD 6n5zktFl3BHGFbHhMQkvJ9f4ek4HuCM7y59XCr0rChd, OR7, RR6B, axis 45, toric lens, SN6A T3 26.50D", where "John Doe, 9 Jan. 1955, cataract, 3626EE2F" was encrypted with AES-128 (one hundred and twenty-eight bit Advanced Encryption Standard) with an encryption key of "Qr39Pt7L" to produce "LzEsJkbW8xdf70vF+7wTD6n5zktFl3 BHGF-bHh MQkvJ9f4ek4HuCM7y59XCr0rChd" in a base64 text format. As illustrated, garment 425 may include machine-readable information 460. Machine-readable information 460 may be printed and/or placed on garment before machine-readable information 430 is printed on garment 425. For example, to prevent fraud and/or fraudulent behavior, machine-readable information 460 may be printed and/or placed on garment before delivery to a medical facility that includes medical system 100 (see FIG. 1). A manufacturer of garment 425 may print and/or place machine-readable information 460 upon garment 425.

As illustrated, garment 425 may include orientation information 435 and 440. For example, orientation information 435 can indicate a side of garment 425 that should be oriented towards feet of patient 110, and orientation information 440 may indicate a side of garment 425 that should be oriented towards a head of patient 110 (see FIG. 1). Garment 425 may include other orientation information, as well. As shown, garment 425 may include orientation information 445.

Orientation information may also provide intraoperative guidance to medical personnel during steps in the medical procedure. In one example, orientation information 445a may include written orientation and/or instructions associated with orienting a device and/or implant used in a medical procedure. In another example, orientation information 445b may include a graphic and/or depiction of a device and/or implant used in the medical procedure. As shown, orientation information 445 provides a message and an illustration of a lens to be implanted at a forty-five degree axis.

Figure 5:
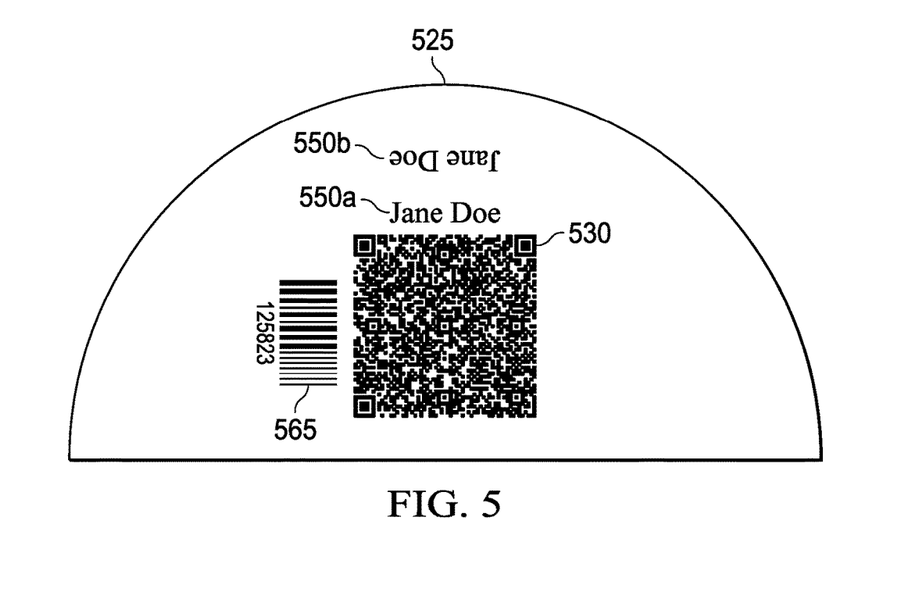
FIG. 5 illustrates a garment embodied as a cap or hat that includes machine-readable information, according to one or more embodiments.

FIG. 5 illustrates a garment 525 embodied as a cap or hat, according to one or more embodiments. As shown, garment 525 may include a name 550 and machine-readable information 530 that is associated with patient 110 (see FIG. 1). Machine-readable information 530 may be or include a two-dimensional barcode. For example, the two-dimensional barcode may be or include a quick response (QR) code.

Machine-readable information 530 may include, for example, one or more of a name, a date of birth, a patient identification code, a resuscitation directive, one or more medical conditions, one or more allergies and/or conditions, a blood type, a type of surgery, a specification within the type of surgery, and an authentication code. For example, machine-readable information 430b may be created from a string, such as a comma-separated value string such as "Jane Doe, 9 Jan. 1955, 10938A45, N, Z91.012-493.20-Z88.0, Z67.31, CABG-36.16, 9e64cd24594fbalbe20975fac6 4201eb". As such, the value "10938A45" may be a patient identification that may be used as an index or key to access a database that stores additional patient information. The value "N" may indicate that a "do not resuscitate" directive is negative, while the value "Z91.012-493.20-Z88.0" may be hyphen-separated values indicating that patient 110 (see FIG. 1) is allergic to eggs (code: Z91.012), has chronic obstructive pulmonary disease (COPD) (code: 493.20), and is allergic to penicillin (code: Z88.0). The value "CABG-36.16" may also include hyphen-separated values indicating that patient 110 is to have a coronary artery bypass grafting (code: CABG) as a double internal mammary-coronary artery bypass (code: 36.16).

An authentication code may be generated via one or more of a checksum and a cryptographic hash function, among others. In one example, the checksum may include a cyclic redundancy check. In another example, the cryptographic hash function may be at least one of a message digest MD-4, MD-5, secure hash algorithm (SHA) 64, SHA-128, and SHA-256, among others. The authentication code may be generated from patient information. For example, the authentication code may be generated from "Jane Doe, 9 Jan. 1955, 10938A45, N, Z91.012-493.20-Z88.0, Z67.31, CABG-36.16". The authentication code may be generated from patient information and a "salt". For example, the "salt" may be a value that is used to alter a checksum and/or a hash such that the original string and the salt are needed to authenticate the original string. The authentication code "9e64cd24594fbalbe20975fac6420leb" may be generated via the MD-5 hash function, the patient information, and a salt of ",PqulZfW2". As such, "9e64cd24594fbalbe20975 fac6420leb" may be generated by using the MD-5 hash function of the string "Jane Doe, 9 Jan. 1955, 10938A45, N, Z91.012-493.20-Z88.0, Z67.31, CABG-36.16, PqulZfW2".

Figure 6:
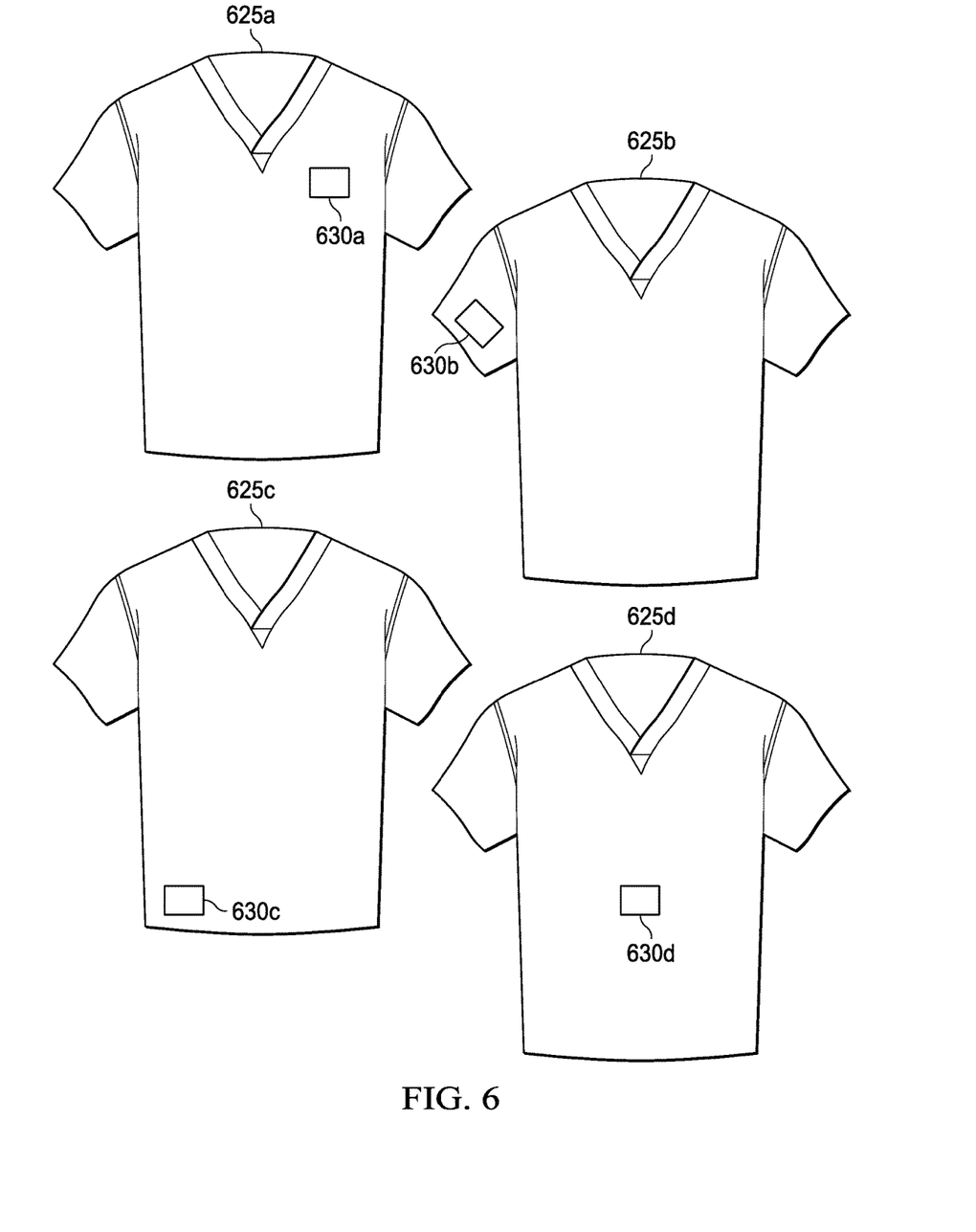
FIG. 6 illustrates garments embodied as scrub shirts that include machine-readable information at various positions, according to one or more embodiments.

FIG. 6 illustrates another garment 625 embodied as a scrub shirt that includes machine-readable information 630, according to one or more embodiments. As shown, garments 625a-625d may have respective machine-readable information 630a-630d printed and/or placed in various places on the respective garment. Machine-readable information 630 may be placed at various positions that may make accessing machine-readable information 630 easier and/or that may depend upon a medical procedure. Machine-readable information 630 may include one or more structures, one or more functionalities, and/or information described with reference to one or more of machine-readable information 130 (see FIG. 1), 430 (see FIG. 4), and 530 (see FIG. 5).

Figure 7:
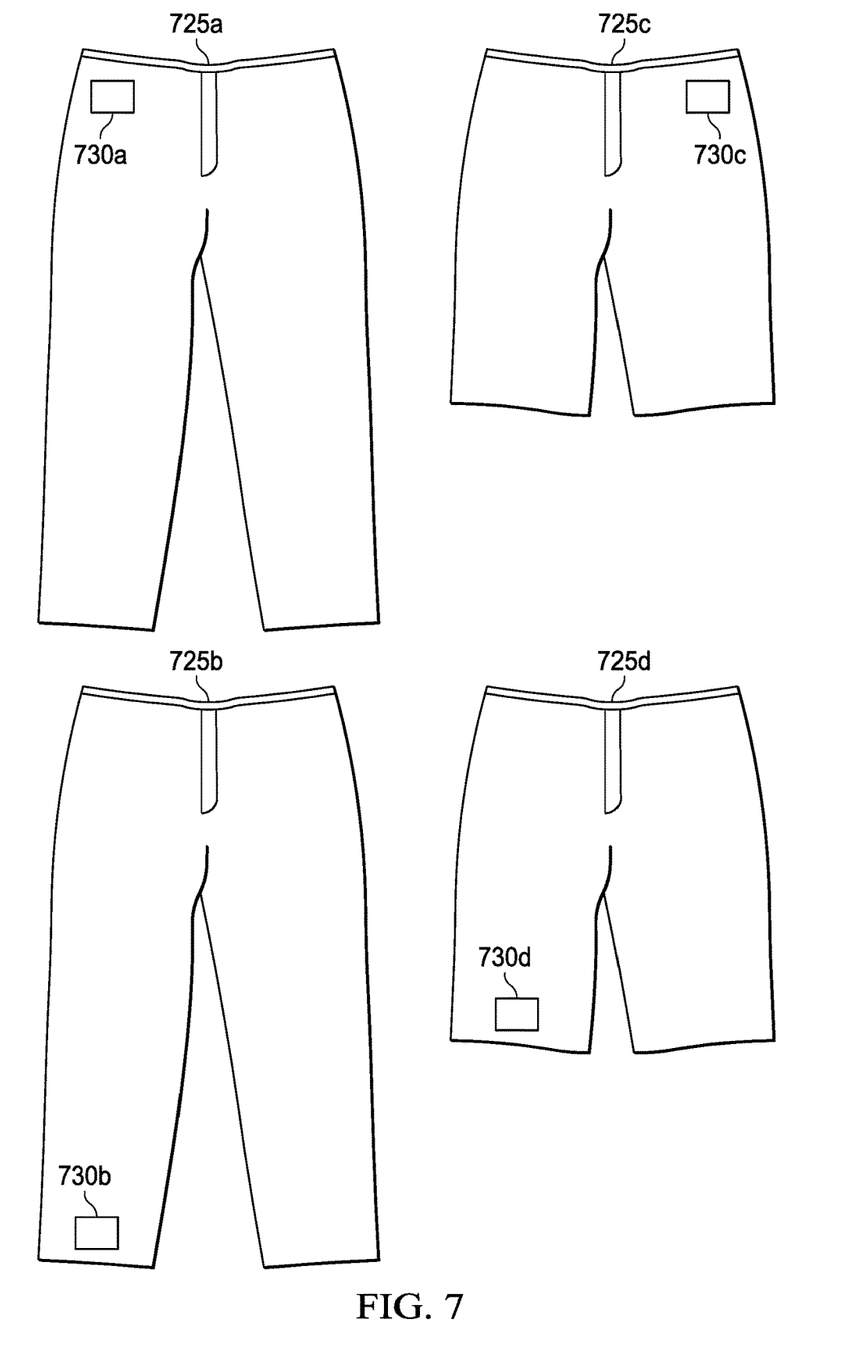
FIG. 7 illustrates garments embodied as scrub pants and exam shorts that include machine-readable information at various positions, according to one or more embodiments.

FIG. 7 also illustrates another garment 725 embodied as scrub pants 725a and 725b and exam shorts 725c and 725d that include machine-readable information 730, according to one or more embodiments. As shown, garments 725a-725d may have respective machine-readable information 730a-730d printed and/or placed in various places on the respective garment. Machine-readable information 730 may be placed at various positions that may make accessing machine-readable information 730 easier and/or that may depend upon a medical procedure. Machine-readable information 730 may include one or more structures, one or more functionalities, and/or information described with reference to one or more of machine-readable information 130 (see FIG. 1), 430 (see FIG. 4), and 530 (see FIG. 5).

Figure 8:
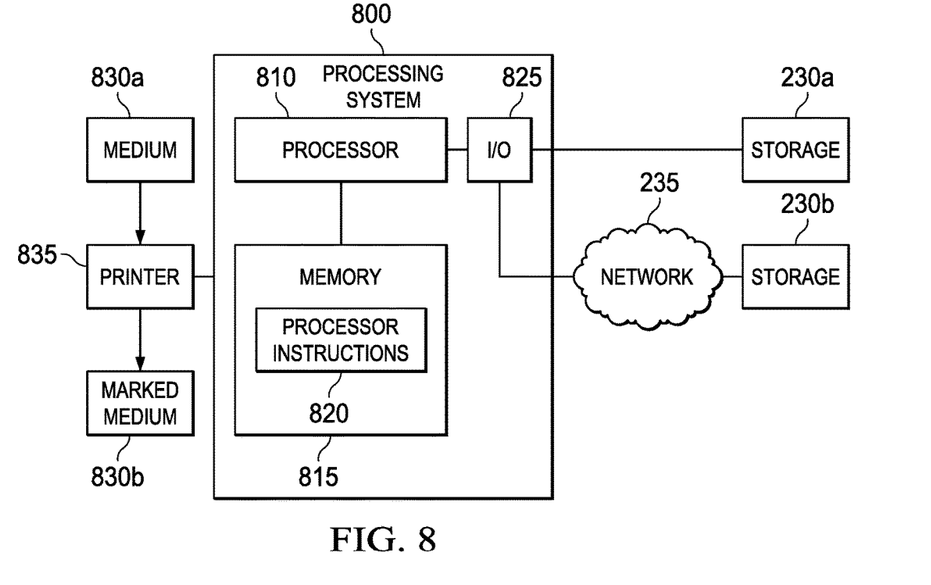
FIG. 8 provides a block diagram of a printing process and system, according to one or more embodiments.

Turning now to FIG. 8, a block diagram of printing process and system is illustrated, according to one or more embodiments. As shown, a processing system 800 may be communicatively coupled to a printer 835. In one example, processing system 800 may be communicatively coupled to printer 835 via wireless communications. In a second example, processing system 800 may be communicatively coupled to printer 835 via wired communications. In another example, processing system 800 may be communicatively coupled to printer 835 via a network. Although processing system 800 and printer 835 are illustrated as separate blocks, system 800 and printer 835 may be combined.

Processing system 800 may include one or more structures and/or one or more functionalities of those described with reference to processing system 200. For example, processing system 800 may include a processor 810, a memory 815 that may be communicatively coupled to processor 810 and that may include processor instructions 820, and an I/O device 825 that may be communicatively coupled to processor 800. Processor 810, memory 815, processor instructions 820, and I/O device 825 may include one or more structures and/or one or more functionalities of those described with processor 210, memory 215, processor instructions 220, and I/O device 225, respectively.

Processing system 800 may be or include any type of processing device. For example, processing system 800 may be or include a PDA, a laptop computer system, a desktop computer system, a server computer system, an embedded processing system, a wireless telephonic device, a tablet computing device, and a mobile computing system, among others.

As shown, processing system 800 may be communicatively coupled to external storage 230a and may be communicatively coupled to external storage 230b via network 235. Storage 230 may store one or more diagnostic images of at least a portion of patient 110 (see FIG. 1) and/or may store one or more reference images of at least a portion of patient 110. In one example, storage 230 may store one or more X-ray images and/or one or more magnetic resonance imaging (MRI) images. In another example, storage 230 may store one or more reference image of an eye of patient 110. Storage 230 may store preoperative measurements. In one example, storage 230 may store electrocardiogram information. In another example, storage 230 may store one or more of a radii, a radii, corneal curvature of steep and flat axes, a limbal position and diameter, a pupil position and diameter, and a corneal reflex position, among others. The preoperative measurements may assist in one or more medical procedures. For example, the preoperative measurements may assist with a number and locations of incisions and an appropriate intraocular lens using one or more formulas in a cataract surgical procedure.

As illustrated, a medium 830*a* may be provided and/or fed to printer 835. Printer 835 may be or include a device, such as printing device, that is operable to print and/or place machine-readable information and/or human-readable information as one or more markings on a medium. For example, printer 835 may mark medium 830*a* with machine-readable information to produce a marked medium 830*b*. Printer 835 may print and/or place one or more optical codes on medium 830*a*, producing marked medium 830*b*. Printer 835 may print and/or place one or more of orientation information and name information, among others, on medium 830*a*, producing marked medium 830*b*. Printer 835 may print and/or place one or more of orientation information 135, 140, 145, 435, 440, and 445 on medium 830*a*, producing marked medium 830*b*. Printer 835 may print and/or place one or more of name information 150, 450, and 550 on medium 830*a*, producing marked medium 830*b*.

Medium 830 may be or include one or more mediums that can be marked with machine-readable information and/or human-readable information. In one example, medium 830 may include one or more of paper, cloth, and plastic, among others. In another example, medium 830 may include one or more of a head band, a cap, a hat, a sticker (e.g., an adhesive-backed sticker), scrub pants, a bandage, a scrub shirt, one or more socks, one or more slippers, a patient gown, an exam cape, exam shorts, and a robe, among others. Medium 830 may be arranged in a manner where printer 835 may print and/or place one or more markings on medium 830. In one example, medium 830 may be folded in a manner where printer 835 may print and/or place one or more markings on medium 830. In another example, one or more portions of medium 830 may be placed in and/or held by a hoop and/or a cartridge where printer 835 may print and/or place one or more markings on medium 830.

Processing system 800 may provide information to printer 835. In one example, processing system 800 may provide information associated with patient 110 (see FIG. 1) to printer 835. Patient information, described herein, may be provided to printer 835 via processing system 800. In a second example, processing system 800 may retrieve one or more portions of information associated with patient 110 from storage 230 and may provide at least a portion of the retrieved information, a key or index associated with the one or more portions of information associated with patient 110, and/or authentication information associated with the one or more portions of information associated with patient 110. Processing system 800 may retrieve preoperative measurements from storage 230 which may be provided to printer 835. A key or index associated with one or more diagnostic images may be determined and/or created and may be provided to printer 835. Authentication information may be determined and/or created to match and/or ensure machine-readable information associated with patient 110 (see FIG. 1) corresponds to storage 230*a*. In another example, processing system 800 may provide machine-readable marking information to printer 835. Machine-readable marking information may include barcode information.

Printer 835 may be located at a medical facility. For example, printer 835 may be located at an office of a doctor, a hospital, an urgent care facility, or an outpatient surgery center, among others. Printer 835 may be located at a manufacturer and/or a distributer. In one example, printing machine-readable information on a garment at the manufacturer and/or the distributer may aid in preventing fraudulent and/or counterfeit garments. In another example, machine-readable information may be printed and/or placed on a garment used in a medical procedure at the manufacturer and/or the distributer, and the machine-readable information may be assigned to a patient. The machine-readable information may be assigned to the patient when the patient is issued the garment, and the machine-readable information assigned to the patient may be used to identify the patient and/or may be used to provide a key to retrieve information associated with the patient.

Figure 9:
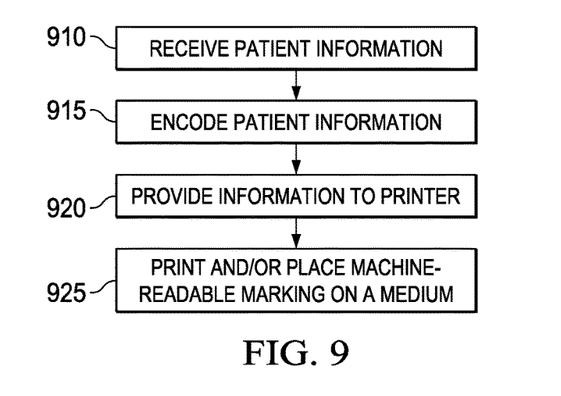
FIG. 9 illustrates a method of providing machine-readable information associated with a medical procedure, according to one or more embodiments.

Turning now to FIG. 9, a method of providing machine-readable information associated with a medical procedure is illustrated, according to one or more embodiments. At step 910, patient information may be received. The patient information may include information pertinent to a medical procedure and/or the patient. For example, the patient information may include one or more of a name, a date of birth, medical procedure information, medical implant information, a food allergy, and a drug allergy, among others. The patient information may be received from a storage device. In one example, the storage device may include a database, and the patient information may be received from the database. In another example, the storage device may include a USB storage device. The patient information may be received from a processing system and/or computing device.

At step 915, patient information may be encoded. In one example, encoding the patient information may include producing a comma separated value (CSV) string from the patient information. In a second example, encoding the patient information may include encrypting one or more portions of the patient information. In a third example, encoding the patient information may include computing a hash and/or a checksum of one or more portions of the patient information. In another example, encoding the patient information may include encoding machine-readable information with the patient information.

Encoding the machine-readable information with the patient information may include producing one or more of a graphic, a raster (e.g., a raster file), a bit-map, a scalar vector graphic, and instructions (e.g., instructions of printer command language program, PostScript instructions, etc.). For example, the one or more of the graphic, the raster, the bit-map, the scalar vector graphic, and the instructions may include barcode information and/or symbols and/or may include data that may be used by printer 835 (see FIG. 8) to print and/or place the barcode information and/or symbols. The barcode information may include a type of barcode. For example, the type of barcode may include codabar, code 25, code 11, farmacode, code 32, code 39, code 49, code 93, code 128, CPC binary, EAN 2, EAN 5, EAN 8, EAN 13, GS1-128, GS1 DataBar, ITF-14, JAN, KarTrak ACI, MSI, Pharmcode, Plessy, PostBar, POSTNET, RM4SCC/KIX, RM Mailmark C, RM Mailmark L, Telepen, Universal Product Code, Aztec Code, Code 1, ColorCode, Color Construct Code, ContoSign, d-touch, DataGlyphs, Data Matrix, Datastrip Code, EZcode, High Capacity Color Barcode, Han Xin Barcode, HueCode, InterCode, MaxiCode, NexCode, PDF417, Qode, QR code, ShotCode, or SPARQCode, among others.

At step 920, the encoded patient information may be provided to a printer. For example, the encoded patient information may be provided to printer 835 (see FIG. 8) via one or more of a wireless communication, a wired communication, and a network communication, among others.

At step 925, machine-readable information may be printed and/or placed on a medium. For example, printer 835 (see FIG. 8) may print and/or place the machine-readable information on medium 830 (see FIG. 8). Printer 835 may print a barcode on medium 830. Printer 835 may print and/or place symbols on medium 830.

The machine-readable information may be printed and/or placed on the medium using a marking material that reflects one or more specific wavelengths of light and/or transforms one or more specific wavelengths of light into other one or more specific wavelengths of light. For example, the machine-readable marking may be printed and/or placed on the medium using an ink that reflects and/or transforms ultraviolet light. The ink may transform ultraviolet light into another wavelength of light that can be acquired via one or more cameras and/or image sensors described herein. The machine-readable information may be printed and/or placed on the medium using a marking material that absorbs one or more specific wavelengths of light.

Figure 10:
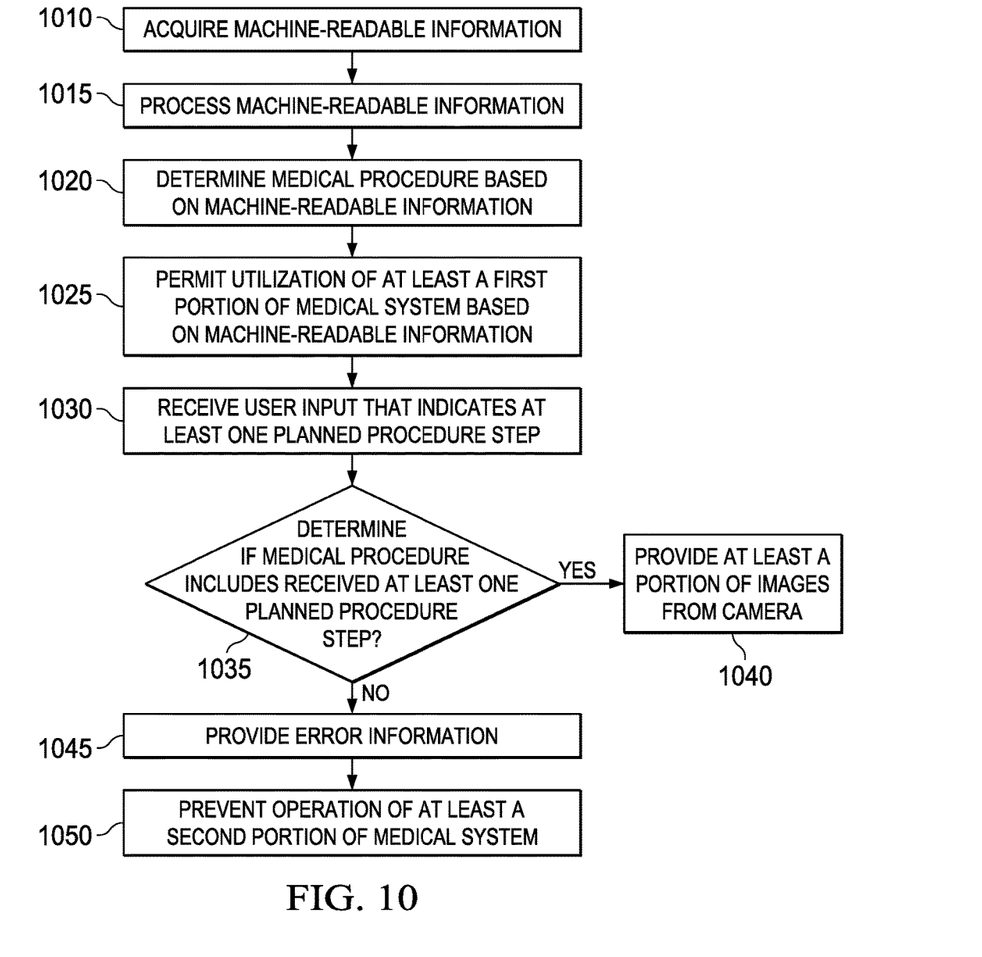
FIG. 10 illustrates a method of processing machine-readable information associated with a patient, according to one or more embodiments.

Turning now to FIG. 10, a method of processing machine-readable information associated with a medical procedure is illustrated, according to one or more embodiments. At step 1010, machine-readable information may be acquired. In one example, acquiring the machine-readable information may include a camera acquiring an image that includes the machine-readable information. A camera of medical system 100 (see FIG. 1) may acquire an image that includes machine-readable information 130 (see FIG. 1). In a second example, portable medical device 300a (see FIG. 3A) may use camera 310 (see FIG. 3A) to acquire an image that includes the machine-readable information. In another example, portable medical device 300b (see FIG. 3B) may use OA device 330 (see FIG. 3B) to acquire the machine-readable information. OA device 330 may acquire one or more of machine-readable information 130, 430 (see FIG. 4), 465 (see FIG. 4), 530 (see FIG. 5), 565 (see FIG. 5), 630 (see FIG. 6), and 730 (see FIG. 7), among others.

At step 1015, the machine-readable information may be processed. Processing the machine-readable information may include processing one or more images to determine information stored via the machine-readable information. For example, the one or more images may include one or more barcodes that include information associated with a medical procedure. The one or more barcodes may include information described herein, and processing the machine-readable information may include retrieving information associated with a medical procedure from the machine-readable information.

The machine-readable information may be processed to determine patient data. In one example, the machine-readable information may include the patient data. In another example, processing the machine-readable information to determine patient data may include retrieving one or more portions of the patient data from a storage device. Storage 230a (see FIG. 2) may store the one or more portions of the patient data, and one or more portions of the machine-readable information may be used to retrieve the one or more portions of the patient data from storage 230a. Storage 230b (see FIG. 2) may store the one or more portions of the patient data, and one or more portions of the machine-readable information may be used to retrieve, via network 235 (see FIG. 2), the one or more portions of the patient data from storage 230b.

The machine-readable information may include encrypted information. For example, processing the machine-readable information to determine patient data may include decrypting information stored via the machine-readable information to determine patient data.

At step 1020, a medical procedure may be determined. For example, the information retrieved from the machine-readable information may indicate the medical procedure. The information retrieved from the machine-readable information 430 (see FIG. 4) may indicate a medical procedure of a cataract surgery. The information retrieved from the machine-readable information 530 (see FIG. 5) may indicate a medical procedure of a coronary artery bypass grafting surgery. Medical system 100 (see FIG. 1) may be operable to be used in multiple medical procedures, and the information retrieved from the machine-readable information may be used to select the medical procedure from the multiple medical procedures for which medical system 100 may be permitted.

At step 1025, use of one or more portions of medical system 100 (see FIG. 1) may be permitted based on the information retrieved from the machine-readable information. In one example, use of microscope 120 (see FIG. 1) and display 155 (see FIG. 1) may be permitted. In a second example, use of display 160 (see FIG. 1) may be permitted to display vital signs of patient 110 (see FIG. 1), though not permitted to provide images acquired via microscope 120. The information retrieved from the machine-readable information may indicate that student medical personnel may not participate in the medical procedure. In another example, use of display 160 may be permitted to provide images acquired via microscope 120 based on one or more indications of the information retrieved from the machine-readable information.

At step 1030, user input that indicates at least one planned procedure step may be received. For example, a medical procedure may incorporate multiple planned procedure steps. The medical procedure may incorporate a surgery that incorporates multiple planned procedure steps.

At step 1035, it may be determined if the medical procedure incorporate s the at least one planned procedure step, received at step 1030. If the medical procedure does incorporate at least one planned procedure step, at least a portion of images acquired via a camera may be provided to a display at step 1040. In one example, the at least the portion of images acquired via the camera may be provided to at least one of displays 155 and 160 (see FIG. 1). In another example, microscope 120 (see FIG. 1) may include a display, and the at least the portion of images acquired via the camera may be provided to the display of microscope 120. Microscope 120 may include a display that augments one or more views of one or more objects. For example, providing, to the display, may include augmenting the one or more views of the one or more objects.

If the medical procedure does not incorporate the at least one planned procedure step, error information may be provided to a display at step 1045. In on example, the error information may be provided to at least one of displays 155 and 160 (see FIG. 1). In a second example, microscope 120 (see FIG. 1) may include a display, and the error information may be provided to the display of microscope 120. In another example, the error information may be provided to a display that augments one or more views, via microscope 120 (see FIG. 1), of one or more objects.

Operation of at least a second portion of the medical system may be prevented if the medical procedure does not incorporate the at least one planned procedure step, at step 1050. For example, preventing use of the at least the second portion of the medical system may aid in preventing error or further error in the medical procedure. The at least the second portion of the medical system may be different from the at least the first portion of the medical system, permitted at step 1025. The at least the second portion of the medical system may be the at least the first portion of the medical system, permitted at step 1025. For example, the at least the first portion of the medical system may be disabled if the medical procedure does not incorporate the at least one planned procedure step.

Preventing operation of the at least the second portion of the medical system may be overridden. In one example, the prevention of the at least the second portion of the medical system may be overridden for life and/or limb saving purposes. In a second example, one or more portions of the medical procedure may be experimental. The experimental one or more portions of the medical procedure may not be incorporate d in stored protocol for a medical procedure. In another example, total control of the medical system may not be withheld from one or more medical personnel.

Figure 11:
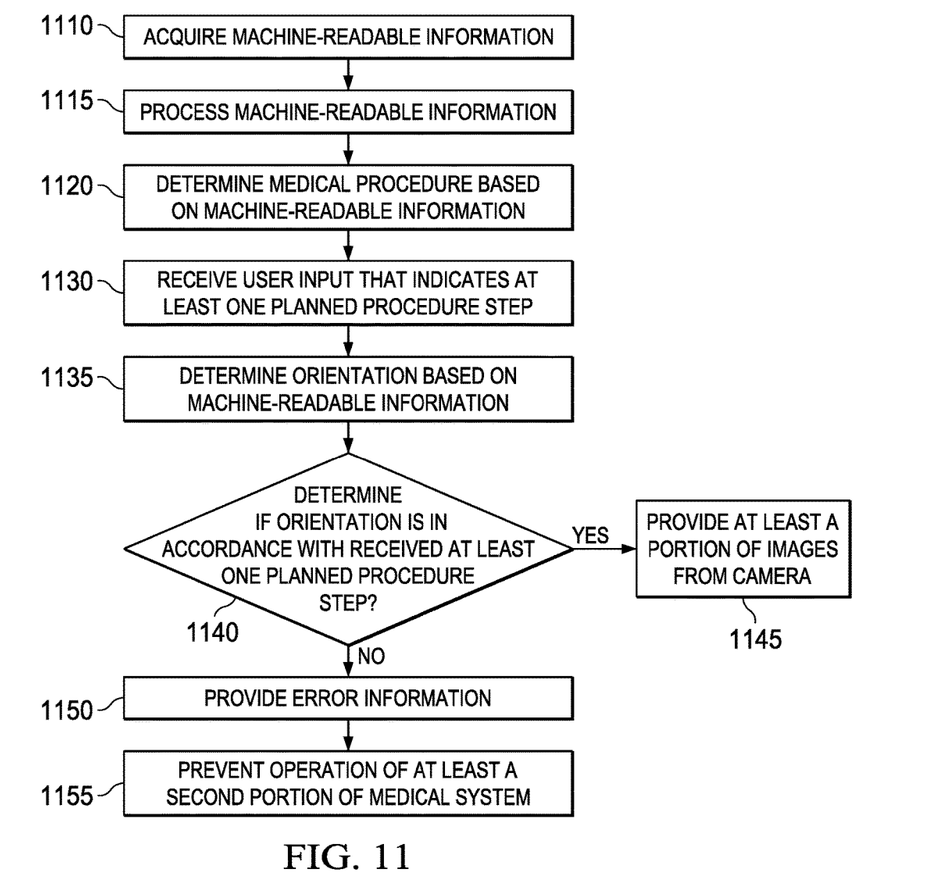
FIG. 11 illustrates a method of processing machine-readable information associated with a patient and an orientation of the machine-readable information, according to one or more embodiments.

Turning now to FIG. 11, a method of processing machine-readable information associated with a medical procedure and an orientation of the machine-readable information is illustrated, according to one or more embodiments. Steps 1110-1130 may be performed in accordance with steps 1010-1030 (see FIG. 10), respectively.

At step 1135, an orientation based on machine-readable information may be determined. The information retrieved from the machine-readable information may include and/or indicate an orientation. For example, the one or more portions of medical system 100 (see FIG. 1) may be permitted or disabled based on the orientation. The orientation may be relative to a portion of medical system 100 (see FIG. 1), such as microscope 120 (see FIG. 1), and the one or more portions of medical system 100 may be permitted or disabled based on the orientation relative to the portion of medical system 100.

At step 1140, it may be determined if the determined orientation is in accordance with the at least one planned procedure step. If the determined orientation is in accordance with the at least one planned procedure step, at least a portion of images acquired via a camera may be provided to a display at step 1145. Step 1145 may be performed in accordance with step 1040 (see FIG. 10). If the determined orientation is not in accordance with the at least one planned procedure step, error information may be provided to a display at step 1150. Steps 1150 and 1155 may be performed in accordance with respective steps 1045 and 1050, respectively.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system, comprising:
 a printing device operable to print machine-readable information upon a garment to be worn by a patient during an ocular medical procedure, the machine-readable information to be printed on the garment comprising:
  orientation information for orienting the garment relative to a body part of the patient for aligning the patient relative to a portion of a medical system; and
  instructions associated with orienting a device or an implant used in the ocular medical procedure;
 a processor communicatively coupled to the printing device; and
 a memory, coupled to the processor, that stores instructions executable by the processor;
 wherein, as the processor executes the instructions, the system is operable to:
  receive patient information associated with the patient;
  encode the patient information, producing encoded patient information; and
  place the machine-readable information, based on the encoded patient information, on the garment to be worn by the patient during the ocular medical procedure.

2. The system of claim 1, wherein the machine-readable information comprises a barcode.

3. The system of claim 2, wherein the barcode is a two-dimensional barcode.

4. The system of claim 1, wherein:
 when the system encodes the patient information, producing the encoded patient information, the system is operable to produce at least one of a graphic, a raster, a bit-map, a scalar vector graphic, and instructions; and
 as the processor executes the instructions, the system is further operable to:
  provide the at least one of the graphic, the raster, the bit-map, the scalar vector graphic, and the instructions to the printing device to print, based on the at least one of the graphic, the raster, the bit-map, the scalar vector graphic, and the instructions, the machine-readable information, based on the encoded patient information, on the garment to be worn by the patient during the medical procedure.

5. The system of claim 1, wherein the machine-readable information comprises information that specifies the ocular medical procedure.

6. The system of claim 1, wherein the machine-readable information comprises preoperative measurements.

7. The system of claim 1, wherein, when the system encodes the patient information, producing the encoded patient information, the system is operable to encrypt at least a portion of the patient information.

8. The system of claim 1, wherein, as the processor executes the instructions, the system is further operable to:
 print, via the printing device, intraoperative guidance information, based on the patient information, on the garment to be worn by the patient during the medical procedure.

9. The system of claim 8, wherein the intraoperative guidance information comprises at least one of a graphic and a depiction of the device or the implant to be used in the ocular medical procedure.

10. A method of printing a garment to be worn during a medical procedure, the method comprising:
 receiving patient information and orientation information associated with a patient, the machine-readable information comprising:

the orientation information for orienting the garment relative to a body part of the patient for aligning the patient relative to a portion of a medical system; and
instructions associated with orienting a device or implant used in an ocular medical procedure;
encoding the patient information and the orientation information, producing encoded patient information; and
printing, by a printing device, the machine-readable information, based on the encoded patient information, on a garment to be worn by the patient during a medical procedure.

11. The method of claim 10, wherein the machine-readable information comprises a barcode.

12. The method of claim 11, wherein the barcode is a two-dimensional barcode.

13. The method of claim 10, wherein the encoding the patient information, producing the encoded patient information, comprises producing at least one of a graphic, a raster, a bit-map, a scalar vector graphic, and instructions;
the method further comprising:
providing the at least one of the graphic, the raster, the bit-map, the scalar vector graphic, and the instructions to the printing device to print, based on the at least one of the graphic, the raster, the bit-map, the scalar vector graphic, and the instructions, the machine-readable information, based on the encoded patient information, on the garment to be worn by the patient during the medical procedure.

14. The method of claim 10, wherein the machine-readable information comprises information that specifies the ocular medical procedure.

15. The method of claim 10, wherein the machine-readable information comprises preoperative measurements.

16. The method of claim 10, wherein the encoding the patient information, producing the encoded patient information, comprises encrypting at least a portion of the patient information.

17. The method of claim 10, further comprising:
disposing intraoperative guidance information, based on the patient information, on the garment to be worn by the patient during the medical procedure.

18. The method of claim 17, wherein the intraoperative guidance information comprises at least one of a graphic and a depiction of the device or the implant to be used in the ocular medical procedure.

* * * * *